(12) United States Patent
Golden et al.

(10) Patent No.: US 9,364,467 B2
(45) Date of Patent: Jun. 14, 2016

(54) RIFAXIMIN DERIVATIVE AND USES THEREOF

(71) Applicants: Salix Pharmaceuticals, Ltd, Raleigh, NC (US); Alfa Wassermann S.P.A., Bologna (IT)

(72) Inventors: Pam Golden, Durham, NC (US); Mohammed A. Kabir, Cary, NC (US); Giuseppe Claudio Viscomi, Bologna (IT); Manuela Campana, Bologna (IT); Donatella Confortini, Bologna (IT); Miriam Barbanti, Bologna (IT)

(73) Assignees: Salix Pharmaceuticals, Ltd., Bridgewater, NJ (US); Alfa Wassermann S.P.A., Bologna (IT)

( * ) Notice: Subject to any disclaimer, the term of this patent is extended or adjusted under 35 U.S.C. 154(b) by 0 days.

(21) Appl. No.: 14/707,858

(22) Filed: May 8, 2015

(65) Prior Publication Data
US 2015/0342934 A1 Dec. 3, 2015

Related U.S. Application Data

(63) Continuation of application No. 14/319,060, filed on Jun. 30, 2014, now Pat. No. 9,035,046, which is a continuation of application No. PCT/US2013/023110, filed on Jan. 25, 2013.

(60) Provisional application No. 61/590,516, filed on Jan. 25, 2012.

(51) Int. Cl.
| | | |
|---|---|---|
| *A61K 31/437* | (2006.01) | |
| *A61K 45/06* | (2006.01) | |
| *C07D 491/22* | (2006.01) | |
| *C07D 498/22* | (2006.01) | |

(52) U.S. Cl.
CPC .............. *A61K 31/437* (2013.01); *A61K 45/06* (2013.01); *C07D 491/22* (2013.01); *C07D 498/22* (2013.01)

(58) Field of Classification Search
CPC ............................ A61K 31/437; A61K 45/06
See application file for complete search history.

(56) References Cited

U.S. PATENT DOCUMENTS

| 4,188,321 | A | 2/1980 | Maggi et al. |
|---|---|---|---|
| 4,341,785 | A | 7/1982 | Marchi et al. |
| 2003/0009022 | A1 | 1/2003 | Klein et al. |
| 2008/0009487 | A1 | 1/2008 | Sternlicht |
| 2009/0028940 | A1 | 1/2009 | Jahagirdar et al. |
| 2009/0082558 | A1 | 3/2009 | Kothakonda et al. |
| 2009/0093415 | A1 | 4/2009 | Yamano |
| 2011/0065740 | A1 | 3/2011 | Forbes et al. |
| 2011/0105550 | A1 | 5/2011 | Gushurst et al. |
| 2011/0178113 | A1 | 7/2011 | Forbes et al. |
| 2011/0294726 | A1 | 12/2011 | Pimentel et al. |
| 2012/0077835 | A1 | 3/2012 | Selbo et al. |
| 2012/0214833 | A1 | 8/2012 | Kulkarni et al. |

OTHER PUBLICATIONS

Di Stefano, et al., "Systemic Absorption of Rifamycin SV MMX Administered as Modified-Release Tablets in Healthy Volunteers," Antimicrobial Agents and Chemotherapy, 2011, vol. 55(5), pp. 2122-2128.

Aristoff, et al., "Rifamycins—Obstacles and Opportunities," Tuberculosis, 2010, vol. 90, pp. 94-118.

Selva, et al., "Rifamycins, Antibacterial Antibiotics and Their New Applications," Analogue-Based Drug Discovery II, Fishcer, et al., Ed., Wiley-VCH, 2010, pp. 173-187.

Rastogi, et al., "Activity of Rifapentine and its Metabolite 25-O-Desacetylrifapentine Compared with Rifampicin and Rifabutin Against *Mycobacterium tuberculosis, Mycobacterium africanum, Mycobacterium bovis* and *M.bovis* BCG," Journal of Antimicrobial Chemotherapy, 2000, vol. 46, pp. 565-570.

*Primary Examiner* — Bruck Kifle
(74) *Attorney, Agent, or Firm* — McCarter & English, LLP; Jonathan M. Sparks; Michael J. DeGrazia

(57) ABSTRACT

25-desacetyl rifaximin or a pharmaceutically acceptable salt thereof is provided. Methods of treatment of bowl related disorders using isolated and/or purified 25-desacetyl rifaximin or a pharmaceutically acceptable salt thereof are also provided.

8 Claims, No Drawings

RIFAXIMIN DERIVATIVE AND USES THEREOF

RELATED APPLICATIONS

This application is a continuation of U.S. application Ser. No. 14/319,060, filed Jun. 30, 2014, which is a continuation of International Application No. PCT/US2013/023110, filed Jan. 25, 2013, which claims the benefit of U.S. Provisional Application No. 61/590,516, filed Jan. 25, 2012, the entire contents of which are expressly incorporated herein by reference.

BACKGROUND

The number of species and strains of bacteria resistant to antibiotics and the number of antibiotics to which they are resistant has increased world-wide. As a result, infections that had been readily treatable by antibiotics may no longer be so. Increased resistance of bacterial infections to antibiotic treatment has now become a generally recognized medical problem.

Throughout the developed world there is public and governmental concern about the increasing prevalence of antimicrobial resistance to antibiotic therapy in bacteria that cause diseases in humans. Many pathogens exist for which there are few effective treatments, and the number of strains resistant to available drugs is continually increasing. New antimicrobial agents and improved methods are thus needed for the treatment and prevention of infections by such pathogens.

SUMMARY

Provided herein is a 25-desacetyl rifaximin and methods of using the same for the treatment of at least one bowel related disorder. Bowel related disorders, include, for example, irritable bowel syndrome, travelers' diarrhea, small intestinal bacterial overgrowth, Crohn's disease, chronic pancreatitis, pancreatic insufficiency, hepatic encephalopathy, pouchitis, enteritis and colitis (including, ulcerative colitis) and other related conditions. In certain embodiments, the 25-desacetyl rifaximin is isolated and/or purified.

Embodiments relate to a purified and/or isolated 25-desacetyl rifaximin or a pharmaceutically acceptable salt thereof.

Embodiments also relate to a purified and/or isolated 25-desacetyl rifaximin having the formula:

[Chemical structure of 25-desacetyl rifaximin]

Embodiments are directed to pharmaceutical compositions comprising 25-desacetyl rifaximin or a pharmaceutically acceptable salt thereof.

In some embodiments, 25-desacetyl rifaximin is 50%-99.9% pure or purified.

In some embodiments, 25-desacetyl rifaximin is 90% pure or purified.

In some embodiments, 25-desacetyl rifaximin is 95% pure or purified.

In some embodiments, 25-desacetyl rifaximin is from between about 50% to about 99.9% pure or purified.

In some embodiments, a 25-desacetyl rifaximin composition is formulated as one or more of a tablet, caplet, capsule, or liquid dosage form.

Embodiments are directed to methods for treating or preventing one or more bowel related disorders, comprising administering to a subject in need thereof a therapeutically effective amount of 25-desacetyl rifaximin or a pharmaceutically acceptable salt thereof.

In some embodiments, the one or more bowel related disorders comprise irritable bowel syndrome, travelers' diarrhea, small intestinal bacterial overgrowth, Crohn's disease, pancreatitis, pancreatic insufficiency, peritonitis, hepatic encephalopathy, pouchitis, infectious diarrhea, inflammatory bowel disease, diverticular disease, *Clostridium*, *C. difficile* disease, *H. pylori* infection, enteritis, colitis, ulcerative colitis, and bacterial periodontal conditions.

In some embodiments, the traveler's diarrhea is caused by exposure to one or more enteric pathogens.

In some embodiments, the one or more enteric pathogens comprise *Salmonella* spp., *Shigella* spp., *Campylobacter* spp., *Aeromonas*, *Plesiomonas*, *Vibro* spp., *Yersinia entercolitica*, *E. coli*, Enterotoxigenic *Escherichia coli* (ETEC), *E. coli* 0157:H7, *C. difficile* or *H. pylori*.

In some embodiments, the enteric pathogens comprise one or more of a gram-positive bacteria, a gram-negative bacteria, an aerobic bacteria or an anaerobic bacteria.

In some embodiments, *E. coli* comprises enterotoxigenic and/or enteroaggregative strains.

In some embodiments, the methods further comprise administering rehydration therapy (RT) to the subject.

In some embodiments, the RT is administered before, during and/or after the administration of the 25-desacetyl rifaximin.

In some embodiments, the RT comprises one or more of oral rehydration therapy or intravenous rehydration therapy.

Embodiments relate to methods for alleviating the symptoms of bloating, abdominal pain, gas or flatulence in a subject comprising administering to a subject in need thereof a therapeutically effective amount of 25-desacetyl rifaximin or a pharmaceutically acceptable salt thereof.

Embodiments are also directed to methods of treating disorders caused by abnormal GI flora comprising administering to a subject in need thereof a therapeutically effective amount of 25-desacetyl rifaximin or a pharmaceutically acceptable salt thereof.

In some embodiments, the abnormal GI flora comprises one or more of enteropathogenic *E. coli* (EPEC), enterotoxigenic *E. coli* (ETEC), *Shigella* spp., *Salmonella* spp., *Campylobacter* spp., *Vibrio*, *H. pylori*, *Staphylococcus* spp., and *C. difficile*.

Embodiments are directed to kits comprising 25-desacetyl rifaximin and instructions for use.

Embodiments are also directed to methods for treating or preventing traveler's diarrhea in a subject comprising administering to a subject in need thereof a therapeutically effective amount of 25-desacetyl rifaximin or a pharmaceutically acceptable salt thereof. In particular aspects, the traveler's diarrhea to be treated is caused by exposure to *E. coli*.

Embodiments relate to methods for treating or preventing hepatic encephalopathy in a subject comprising administering to a subject in need thereof a therapeutically effective amount of 25-desacetyl rifaximin or a pharmaceutically acceptable salt thereof.

Embodiments also relate to methods for alleviating the symptoms of bloating, gas or flatulence in a subject comprising administering to a subject in need thereof a therapeutically effective amount of 25-desacetyl rifaximin or a pharmaceutically acceptable salt thereof.

Embodiments are directed to methods for treating irritable bowel syndrome in a subject comprising administering to a subject in need thereof a therapeutically effective amount of 25-desacetyl rifaximin or a pharmaceutically acceptable salt thereof.

In some embodiments, the 25-desacetyl rifaximin or pharmaceutically acceptable salt thereof is administered orally. In some embodiments, the 25-desacetyl rifaximin or pharmaceutically acceptable salt thereof is administered topically. In some embodiments, the topically administered 25-desacetyl rifaximin or pharmaceutically acceptable salt thereof is administered in a cream, enema, ointment, lotion, or gel.

Embodiments are also directed to the use of 25-desacetyl rifaximin as a metabolite of rifaximin. In some embodiments, rifaximin is administered to a subject in need of treatment for a bacterial infection in an amount that results in a therapeutically effective amount of 25-desacetyl rifaximin in the subject.

Embodiments relate to methods for treating a bowel related disorder by administering a metabolite of rifaximin to a subject in need of treatment therefore.

Embodiments are also related to methods of inhibiting bombesin BB1 comprises administering 25-desacetyl rifaximin.

Embodiments also relate to methods of inhibiting N-formyl peptide receptor FPR1 comprises administering 25-desacetyl rifaximin.

Embodiments are directed to methods for treating or preventing one or more skin or mucous membrane infections, comprising administering to a subject in need thereof a therapeutically effective amount of 25-desacetyl rifaximin or a pharmaceutically acceptable salt thereof.

In some embodiments, one or more skin or mucous membrane infections comprise vaginal infections, ear infections, lung infections, periodontal conditions, rosacea, and other infections of the skin and/or other related conditions.

Embodiments are also directed to a method for making 25-desacetyl rifaximin by reacting rifaximin with methanol (MeOH) and sodium hydroxide (NaOH). In one aspect the NaOH is 2N NaOH.

DETAILED DESCRIPTION

Provided herein is a rifaximin derivative 25-desacetyl rifaximin having the formula:

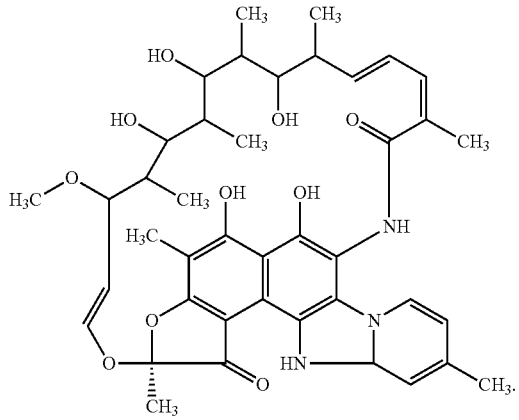 [SMILES: COC1/C=C/O[C@@]2(C)Oc3c(C)c(O)c4c(O)c(c5c(c4c3C2=O)NC2C=C(C)C=CN52)NC(=O)/C(C)=C\C=C\C(C)C(O)C(C)C(O)C(C)C(O)C1C]

The 25-desacetyl rifaximin provided herein is a rifaximin derivative and biological metabolite. Rifaximin (INN; see The Merck Index, XIII Ed., 8304) is an antibiotic pertaining to the rifamycin class, specifically it is a pyrido-imidazo rifamycin which is described and claimed in the Italian Patent IT 1154655. European Patent EP 0161534 describes and claims a process for its production starting from rifamycin O (The Merck Index, XIII Ed., 8301). Rifaximin is currently used in the treatment of traveler's diarrhea and hepatic encephalopathy.

Also provided are pharmaceutically acceptable salts, which include those in which 25-desacetyl rifaximin functions as an acid and is reacted with an appropriate base to form, e.g., sodium, potassium, calcium, magnesium, ammonium, and chorine salts. Those skilled in the art will further recognize that acid addition salts of the claimed compounds can be prepared by reaction of 25-desacetyl rifaximin the appropriate inorganic or organic acid via any of a number of known methods. Alternatively, alkali and alkaline earth metal salts of acidic 25-desacetyl rifaximin are prepared by reacting the 25-desacetyl rifaximin with the appropriate base via a variety of known methods.

Representative salts of 25-desacetyl rifaximin include, for example, nontoxic salts and the quaternary ammonium salts which are formed, for example, from inorganic or organic acids or bases by means well known in the art. Pharmaceutically acceptable acid addition salts of the 25-desacetyl rifaximin include, for example, salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts can include sulfate, pyrosulfate, bisulfate, sulfite, bisulfite, nitrate, phosphate, monohydrogenphosphate, dihydrogenphosphate, metaphosphate, pyrophosphate, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," Journal of Pharmaceutical Science, 1977; 66:1-19). The acid addition salt of 25-desacetyl rifaximin can be prepared by contacting the free base form with a sufficient amount of the desired acid to produce the salt.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., supra., 1977). The base addition salts of the acidic compounds are prepared by contacting the free acid form with a sufficient amount of the desired base to produce the salt. Additionally, basic nitrogen containing groups can be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

A solvate includes, for example, a complex of a solvent and 25-desacetyl rifaximin in the solid state. Exemplary solvates would include, for example, complexes of a compound with ethanol or methanol.

The term "subject" refers to animals such as mammals, including, for example, primates (e.g., humans), cows, sheep, goats, horses, dogs, cats, rabbits, rats, mice and the like. In certain embodiments, the subject is a human.

It is also to be understood that the terminology used herein is for purposes of describing particular embodiments only, and is not intended to be limiting. As used in the specification and the appended claims, the singular forms "a", "an", and "the" include plural referents unless the context clearly indicates otherwise.

Unless otherwise defined, all technical and scientific terms used herein have the same meaning as commonly understood by one of ordinary skill in the art. All publications, patent applications, patents, and other references mentioned herein are incorporated by reference.

Treatment of Skin or Mucous Membrane Infections

Described herein are methods of using 25-desacetyl rifaximin to treat vaginal infections, ear infections, lung infections, periodontal conditions, rosacea, and other infections of the skin and/or other related conditions.

Provided herein are vaginal pharmaceutical compositions to treat vaginal infection, particularly bacterial vaginosis, to be administered topically, including vaginal foams and creams, containing a therapeutically effective amount of 25-desacetyl rifaximin, preferably between about 50 mg and 2500 mg.

Pharmaceutical compositions known to those of skill in the art for the treatment of vaginal pathological conditions by the topical route can be advantageously used with 25-desacetyl rifaximin. For example, vaginal foams, ointments, creams, gels, ovules, capsules, tablets and effervescent tablets can be effectively used as pharmaceutical compositions containing 25-desacetyl rifaximin, which can be administered topically for the treatment of vaginal infections, including bacterial vaginosis.

Also provided herein are method of using 25-desacetyl rifaximin to treat gastric dyspepsia, including gastritis, gastroduodenitis, antral gastritis, antral erosions, erosive duodenitis and peptic ulcers. These conditions can be caused by the *Helicobacter pylori*. Pharmaceutical formulations known by those of skill in the art with the benefit of this disclosure to be used for oral administration of a drug can be used.

Provided herein are methods of treating ear infections with 25-desacetyl rifaximin. Ear infections include external ear infection, or a middle and inner ear infection. Also provided herein are methods of using 25-desacetyl rifaximin to treat or prevent aspiration pneumonia and/or sepsis, including the prevention of aspiration pneumonia and/or sepsis in patients undergoing acid suppression or undergoing artificial enteral feedings via a Gastrostomy/Jejunostomy or naso/oro gastric tubes; prevention of aspiration pneumonia in patients with impairment of mental status, for example, for any reason, for subjects undergoing anesthesia or mechanical ventilation that are at high risk for aspiration pneumonia. Provided herein are methods to treat or to prevent periodontal conditions, including plaque, tooth decay and gingivitis. Provided herein are methods of treating rosacea, which is a chronic skin condition involving inflammation of the cheeks, nose, chin, forehead, or eyelids.

Treatment of Bowel Related Disorders

In some embodiments, provided herein are methods of treating, preventing, or alleviating bowel related disorders. Such methods include administering to a subject in need thereof an effective amount of 25-desacetyl rifaximin or a pharmaceutically acceptable salt, solvate or hydrate thereof. Bowel related disorders include, for example, one or more of irritable bowel syndrome (IBS), diarrhea, microbe associated diarrhea, infectious diarrhea, *Clostridium, Clostridium difficile* disease, travelers' diarrhea, small intestinal bacterial overgrowth (SIBO), Crohn's disease, diverticular disease, pancreatitis (including chronic), pancreatic insufficiency, enteritis, colitis (including, ulcerative colitis), antibiotic associated colitis, hepatic encephalopathy (or other diseases which lead to increased ammonia levels), gastric dyspepsia, cirrhosis, polycystic liver disease, pouchitis, peritonitis, inflammatory bowel disease, *H. pylori* infection. In one embodiment, the subject is suffering from at least one bowel related disorder selected from irritable bowel syndrome, travelers' diarrhea, small intestinal bacterial overgrowth, Crohn's disease, chronic pancreatitis, pancreatic insufficiency, enteritis and colitis.

In some embodiments, provided herein are methods of treating, preventing, or alleviating bowel related disorders in a subject suffering from hepatic insufficiency. Such methods include administering to a subject in need thereof an effective amount of 25-desacetyl rifaximin or a pharmaceutically acceptable salt, solvate or hydrate thereof. A subject "suffering from hepatic insufficiency" as used herein includes subjects diagnosed with a clinical decrease in liver function, for example, due to hepatic encephalopathy, hepatitis, or cirrhosis. Hepatic insufficiency can be quantified using any of a number of scales including a model end stage liver disease (MELD) score, a Child-Pugh score, or a Conn score.

In some embodiments, provided herein are methods for treating or preventing traveler's diarrhea in a subject. Traveler's diarrhea refers to gastrointestinal illness common amongst travelers. According to the CDC, travelers' diarrhea (TD) is the most common illness affecting travelers. Each year between 20%-50% of international travelers, an estimated 10 million persons, develop diarrhea. The onset of travelers' diarrhea usually occurs within the first week of travel but can occur at any time while traveling, and even after returning home. Risk is often dependent on destination though other risk factors are possible. For examples of the use of rifaximin to treat Travelers' diarrhea, see Infante R M, et al. 2004. *Clinical Gastroenterology and Hepatology* 2:135-138 and Steffen R, M. D. et al. 2003. *The American Journal of Gastroenterology* 98(5), each of which is incorporated herein by reference in its entirety.

The illness usually results in increased frequency, volume, and weight of stool. Altered stool consistency also is common A traveler can experience, for example, four to five loose or watery bowel movements each day. Other commonly associated symptoms are nausea, vomiting, diarrhea, abdominal cramping, bloating, fever, urgency, and malaise. Most cases are benign and resolve in 1-2 days without treatment, and TD is rarely life-threatening. The natural history of TD is that 90% of cases resolve within 1 week, and 98% resolve within 1 month.

Infectious agents are the primary cause of TD. The majority of cases are caused by bacterial, viral or protozoan infection. Bacterial enteropathogens cause approximately 80% of TD cases. The most common causative agent isolated in countries surveyed has been enterotoxigenic *Escherichia coli* (ETEC). ETEC produce watery diarrhea with associated cramps and low-grade or no fever. Besides ETEC and other bacterial pathogens, a variety of viral and parasitic enteric pathogens also are potential causative agents. In some embodiments, the traveler's diarrhea is caused by exposure to *E. Coli*.

In some embodiments, provided herein are methods for treating or preventing hepatic encephalopathy in a subject. Hepatic encephalopathy (portal-systemic encephalopathy, liver encephalopathy, hepatic coma) is a deterioration of brain function that occurs because toxic substances normally removed by the liver build up in the blood and reach the brain. Substances absorbed into the bloodstream from the intestine pass through the liver, where toxins are normally removed. In hepatic encephalopathy, toxins are not removed because liver function is impaired. Once in brain tissue, the compounds produce alterations of neurotransmission that affect consciousness and behavior. There are 4 progressive stages of impairment associated with HE that are defined by using the West Haven criteria (or Conn score) which range from Stage 0 (lack of detectable changes in personality) to Stage 4 (coma, decerebrate posturing, dilated pupils). In the earliest stages, the person's mood may change, judgment may be impaired, and normal sleep patterns may be disturbed. As the disorder progresses, the person usually becomes drowsy and confused, and movements become sluggish. Symptoms of hepatic encephalopathy can include impaired cognition, reduced alertness and confusion, a flapping tremor (asterixis), and a decreased level of consciousness including coma (e.g., hepatic coma), cerebral edema, and, possibly, death. Hepatic encephalopathy is commonly called hepatic coma or portal-systemic encephalopathy in the literature.

In some embodiments, provided herein are methods for treating irritable bowel syndrome in a subject. Irritable bowel syndrome (IBS) is a disorder that affects the motility (muscle contractions) of the colon. Sometimes called "spastic colon" or "nervous colitis," IBS is not characterized by intestinal inflammation. IBS is a functional bowel disorder characterized by chronic abdominal pain, discomfort, bloating, and alteration of bowel habits. IBS can begin after an infection (post-infectious, IBS-PI) or without any other medical indicators.

In some embodiments, provided herein are methods for alleviating the symptoms of bloating, gas or flatulence in a subject. In certain embodiments the symptoms of bloating, gas or flatulence are caused by bacterial exposure. In other embodiments, the symptoms of bloating, gas or flatulence are not caused by bacterial exposure.

In some embodiments, provided herein are methods of treating or preventing a pathology in a subject suspected of being exposed to a biological warfare agent.

In some embodiments, treatment of a bowel related disorder includes prophylactic treatment. The identification of subjects who are in need of prophylactic treatment of a bowel related disorder is well within the ability and knowledge of one skilled in the art. Certain of the methods for identification of subjects which are at risk of developing a bowel related disorder (e.g., subjects that can be treated by the methods described herein) are appreciated in the medical arts, such as family history, travel history, expected travel plans and the presence of risk factors associated with the development of that disease state in the subject. A clinician skilled in the art can readily identify such candidate subjects, by the use of, for example, clinical tests, physical examination and medical/family/travel history.

Formulations are provided to a subject in an effective amount. The term "effective amount" includes an amount effective, at dosages and for periods of time necessary, to achieve the desired result without being toxic. In one embodiment, the desired result is inhibiting a virus, or in prolonging the survivability of a subject with such a viral infection. In another embodiment, the desired result is inhibiting a bacterial infection or prolonging the survival of a subject with such a bacterial infection beyond that expected in the absence of such treatment. An effective amount can be provided in one or a series of administrations.

An effective amount of 25-desacetyl rifaximin or a pharmaceutically acceptable salt, solvate or hydrate thereof (e.g., purified or isolated 25-desacetyl rifaximin or a pharmaceutically acceptable salt, solvate or hydrate thereof) can vary according to factors such as the disease state, age, and weight of the subject, and the ability of the compound to elicit a desired response in the subject. An effective amount of 25-desacetyl rifaximin or a pharmaceutically acceptable salt, solvate or hydrate thereof can also vary according to other factors such as intended travel destination of a subject, including but not limited to, Latin America, Africa, the Middle East, and Asia, including both developed, undeveloped and developing areas therein. An effective amount of 25-desacetyl rifaximin or a pharmaceutically acceptable salt, solvate or hydrate thereof can further vary according to other risk-factors a subject may have, including, but not limited to, young age, advanced age, immunosuppression, diagnosis of inflammatory-bowel disease or diabetes, and prior treatment with H-2 blockers or antacids. Dosage regimens can be adjusted to provide the optimum therapeutic response.

The dosage for in vivo therapeutics or diagnostics will generally vary. The effective amount can be determined by a physician on a case-by-case basis and is within the skill of one in the art. Several factors can be taken into account when determining an appropriate dosage. These factors include age, sex and weight of the patient, route of administration, the condition being treated, and the severity of the condition. In some embodiments, suitable dosages and formulations of 25-desacetyl rifaximin or a pharmaceutically acceptable salt, solvate or hydrate thereof can be empirically determined by the administering physician. Standard texts, such as Remington: The Science and Practice of Pharmacy, 17th edition, Mack Publishing Company, and the Physician's Desk Reference, each of which are incorporated herein by reference, can be consulted to prepare suitable compositions and doses for administration. Suitable dosages can also be based upon the text and documents cited herein. A determination of the appropriate dosage is within the skill of one in the art given the parameters for use described herein.

In some embodiments, an effective amount is an amount that is sufficient to palliate, ameliorate, stabilize, reverse or slow the progression of irritable bowel syndrome, diarrhea, microbe associated diarrhea, *Clostridium difficile* associated diarrhea, travelers' diarrhea, small intestinal bacterial overgrowth, Crohn's disease, antibiotic associated colitis, diverticular disease, chronic pancreatitis, pancreatic insufficiency, enteritis, colitis, hepatic encephalopathy, pouchitis, the symptoms of any of the foregoing, or to reduce the symptoms of gas, bloating or flatulence no matter the cause. An effective amount can also be an amount that is sufficient to prevent irritable bowel syndrome, diarrhea, microbe associated diarrhea, *Clostridium difficile* associated diarrhea, travelers' diarrhea, small intestinal bacterial overgrowth, Crohn's disease, chronic pancreatitis, pancreatic insufficiency, enteritis, colitis, hepatic encephalopathy, pouchitis, the symptoms of any of the foregoing, gas, bloating or flatulence.

The dosage of 25-desacetyl rifaximin or a pharmaceutically acceptable salt, solvate or hydrate thereof can vary from about 10 mg to about 10 g per day; about 20 mg to about 5 g per day; about 50 mg to about 1 g per day; about 200 mg to about 2500 mg per day or about 100 mg to about 500 mg per day. Ascertaining dosage ranges is well within the skill of one in the art. The dosage of 25-desacetyl rifaximin or a pharmaceutically acceptable salt, solvate or hydrate thereof can range from about 0.05 to 150 mg/kg of body weight. Ranges intermediate to the above-recited values are also intended to be part of the present teachings. Such dosages can vary, for example, depending on whether multiple administrations are given, tissue type and route of administration, the condition of the individual, the desired objective and other factors known to those of skill in the art. Administrations can be conducted infrequently, or on a regular weekly basis until a desired, measurable parameter is detected, such as diminution of disease symptoms. Administration can then be diminished, such as to a biweekly or monthly basis, as appropriate.

The length of treatment for a bowel related disorder can be from about an hour or two to about a year or more. The length of treatment for a bowel related disorder can be for the remainder of a subject's life. For example, in some embodiments, the length of treatment is about 1 hour, about 2 hours, about 5 hours, about 12 hours, about 1 day, about 2 days, about 3 days, about 5 days, about 15 days, about 1 month, about 2 months, about 3 months, about 6 months, about 9 months or about 1 year. The length of treatment for a particular bowel related disorder will depend, at least in part, on the disorder. For example, travelers' diarrhea may only require treatment duration of 12 to about 72 hours, while Crohn's disease may require treatment durations from about 2 days to 3 months. A treatment for hepatic encephalopathy can be, for example, for the remainder of the subject's life. A treatment for IBS can be intermittent for weeks or months at a time or for the remainder of the subject's life. Dosages can also vary depending on the disease state, as described in more detail herein.

In some embodiments, the 25-desacetyl rifaximin or a pharmaceutically acceptable salt, solvate or hydrate thereof is administered to the subject using a composition that provides sustained delivery of the 25-desacetyl rifaximin or a pharmaceutically acceptable salt, solvate or hydrate thereof to a subject. For example, sustained delivery can be delivery for at least 12 hours, at least 24 hours, at least 36 hours, at least 48 hours, at least one week, at least two weeks, at least three weeks, or at least four weeks after the composition is administered to the subject.

In some embodiments, provided herein are methods for treating or preventing hepatic insufficiency in a subject. Hepatic insufficiency includes diseases and disorders in which a subject has defective functional activity of the liver. Clinically, subjects having hepatic insufficiency have decreased, e.g., statistically significantly decreased, liver function. Hepatic insufficiency often leads to liver failure. One exemplary disease which manifests hepatic insufficiency is hepatic encephalopathy.

In some embodiments, the present teachings also provide methods of assessing the efficacy of the treatment in a subject. Such methods includes determining the pre-treatment level of intestinal bacterial overgrowth by methods known in the art (e.g., hydrogen breath testing, biopsy, sampling of the intestinal bacteria, etc.) and then administering a therapeutically effective amount of 25-desacetyl rifaximin or a pharmaceutically acceptable salt, solvate or hydrate thereof to the subject. After an appropriate period of time (e.g., after an initial period of treatment) from the administration of the compound, e.g., 2 hours, 4 hours, 8 hours, 12 hours, or 72 hours, the level of bacterial overgrowth is determined again. In some embodiments, the level of bacterial overgrowth is determined periodically throughout treatment. For example, the bacterial overgrowth can be checked every few hours, days or weeks to assess the further efficacy of the treatment. A decrease in bacterial overgrowth indicates that the treatment is efficacious. Efficacy of a treatment can be measured as reduction of bacterial overgrowth, or can be measured in terms of a reduction of symptoms associated with the bowel related disorder, a stabilization of symptoms, or a cessation of symptoms associated with a bowel related disorder (for example, a reduction of nausea, bloating, diarrhea, and the like).

The method described can be used to screen or select subjects that can benefit from treatment with 25-desacetyl rifaximin or a pharmaceutically acceptable salt, solvate or hydrate thereof. In some embodiments, the modulation of the bacterial overgrowth is an indication that the subject is likely to have a favorable clinical response to the treatment. In some embodiments, the methods provided herein (e.g., methods of treating a subject suffering from or susceptible to a bowel related disorder) include identifying a subject that can benefit from treatment with 25-desacetyl rifaximin or a pharmaceutically acceptable salt, solvate or hydrate thereof.

The term "administration" or "administering" includes routes of introducing the compound(s) to a subject to perform their intended function. Administration includes systemic administration as well as local administration. Examples of routes of administration which can be used include parenteral, oral, topical, inhalation (such as intranasal or intrapulmonary, e.g., by aerosol), rectal and intradermal (such as intramuscular, intracavity, or transdermal).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

In some embodiments, provided herein are uses of a 25-desacetyl rifaximin or a pharmaceutically acceptable salt, solvate or hydrate thereof in therapy.

In some embodiments, the 25-desacetyl rifaximin can be used for the treatment or prevention of infectious disorders caused by a variety of bacterial organisms, including gram-positive, gram-negative, aerobic and anaerobic bacteria. For example, the 25-desacetyl rifaximin can be used to treat disorders caused by abnormal GI flora, e.g., enteropathogens. Representative enteropathogens include, for example, *E. coli*, including, enteropathogenic *E. coli* (EPEC) and enterotoxigenic *E. coli* (ETEC), *Shigella* spp., *Salmonella* spp., *Campylobacter* spp., *Vibrio*, *H. pylori*, *Staphylococcus* spp., and *C. difficile*.

In some embodiments, a subject is treated with rifaximin which metabolizes into 25-desacetyl rifaximin in the body to yield an effect amount of 25-desacetyl rifaximin to treat the bowel related disorder. In this embodiment, the rifaximin can be incubated in the subject for a sufficient time to yield a predetermined level of the 25-desacetyl rifaximin metabolite. Alternatively, the subject can be treated by direct administration of 25-desacetyl rifaximin.

Embodiments relate to a method of treating one or more bowel related disorders. Bowel related disorder, include, for example, irritable bowel syndrome, travelers' diarrhea, small intestinal bacterial overgrowth, Crohn's disease, pancreatitis, pancreatic insufficiency, peritonitis, hepatic encephalopathy, pouchitis, infectious diarrhea, inflammatory bowel disease, diverticular disease, *Clostridium, C. difficile* disease, *H. pylori* infection, enteritis and colitis and other related conditions.

Other disorders that can be treated with 25-desacetyl rifaximin, include, for example, skin infections, bacterial vaginosis, periodontal disease, lung infections, mucosal infections, According to the CDC, Travelers' diarrhea is the most common illness affecting travelers. Each year between 20%-50% of international travelers, an estimated 10 million persons, develop diarrhea. The onset of Travelers' diarrhea can occur within the first week of travel but also can occur at any time while traveling, and even after returning home. Risk is often dependent on destination though other risk factors are possible.

Traveler's diarrhea is marked by increased frequency, volume, and weight of stool. Altered stool consistency also seen in subjects. A traveler can experience, for example, four to five loose or watery bowel movements each day. Other associated symptoms include, for example, nausea, vomiting, diarrhea, abdominal cramping, bloating, fever, urgency, and malaise.

In some embodiments, the methods further comprise administering rehydration therapy (RT) to the subject. The RT can be administered before, during and/or after the administration of the 25-desacetyl rifaximin. RT can include rehydrating the subject in the most efficient or the most tolerated methods. Examples include one or more of oral rehydration therapy or intravenous rehydration therapy.

Hepatic encephalopathy (e.g., portal-systemic encephalopathy, liver encephalopathy, hepatic coma) is a deterioration of brain function that occurs because toxic substances normally removed by the liver build up in the blood and reach the brain. Substances absorbed into the bloodstream from the intestine pass through the liver, where toxins are normally removed. In hepatic encephalopathy, toxins are not removed because liver function is impaired. Symptoms include decreased brain function, reduced alertness and confusion. In the earliest stages, the subject's mood may change, judgment may be impaired, and sleep patterns may be disturbed. As the disorder progresses, the subject can become drowsy and confused, and movements may become sluggish. The hands cannot be held steady when the person stretches out the arms, resulting in a crude flapping motion of the hands (asterixis).

Irritable bowel syndrome (IBS) is a disorder that affects the motility (muscle contractions) of the colon. Sometimes called "spastic colon" or "nervous colitis," IBS is not characterized by intestinal inflammation. IBS is a functional bowel disorder characterized by chronic abdominal pain, discomfort, bloating, and alteration of bowel habits. IBS can begin after an infection (post-infectious, IBS-PI) or without any other medical indicators.

In some embodiments, Travelers' Diarrhea is treated in a subject by administering an effective amount of a 25-desacetyl rifaximin or a pharmaceutically acceptable salt thereof. In some embodiments, the method comprises administering a composition comprising 25-desacetyl rifaximin or a pharmaceutically acceptable salt thereof.

In some embodiments, provided herein are methods for treating or preventing hepatic encephalopathy in a subject comprising administering to a subject in need thereof a therapeutically effective amount of 25-desacetyl rifaximin or a pharmaceutically acceptable salt thereof.

In some embodiments, provided herein are methods for alleviating the symptoms of bloating, gas or flatulence in a subject comprising administering to a subject in need thereof a therapeutically effective amount of 25-desacetyl rifaximin or a pharmaceutically acceptable salt thereof. In some embodiments the symptoms of bloating, gas or flatulence are caused by bacterial exposure. In some embodiments, the symptoms of bloating, gas or flatulence are not caused by bacterial exposure.

In some embodiments, provided herein are methods for treating irritable bowel syndrome in a subject comprising administering to a subject in need thereof a therapeutically effective amount of 25-desacetyl rifaximin or a pharmaceutically acceptable salt thereof.

In some embodiments, 25-desacetyl rifaximin or pharmaceutically acceptable salt thereof can be administered with one or more other additional therapeutic agents.

In some embodiments, the 25-desacetyl rifaximin is administered with an agent for treating inflammatory bowel disease or syndrome which can be optionally employed in combination and can including one or more of sulfasalazine, salicylates, mesalamine, balsalazide, and the like.

For example, 25-desacetyl rifaximin can be administered or formulated in combination with other antibiotics or anti-invectives. For example, they can be administered or formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®), a clarithromycin (e.g., clarithromycin (Biaxin®), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide, rifampin, and rifaximin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin, vancomycin, and tuberin.

25-desacetyl rifaximin can also be administered or formulated in combination with an antiemetic agent. Suitable antiemetic agents include, for example, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

25-desacetyl rifaximin can also be administered or formulated in combination with can be formulated in combination with one or more antiviral agents. Useful antiviral agents include, for example, protease inhibitors, nucleoside reverse transcriptase inhibitors, non-nucleoside reverse transcriptase inhibitors and nucleoside analogs. The antiviral agents include, for example, zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, alpha-interferons; adefovir, clevadine, entecavir, pleconaril.

25-desacetyl rifaximin can also be formulated in combination with an antifungal agent. Suitable antifungal agents include, for example, amphotericin B, itraconazole, ketoconazole, fluconazole, intrathecal, flucytosine, miconazole, butoconazole, clotrimazole, nystatin, terconazole, tioconazole, ciclopirox, econazole, haloprogin, naftifine, terbinafine, undecylenate, and griseofuldin.

25-desacetyl rifaximin can also be administered or formulated in combination with be formulated with aluminum carbonate, aluminum hydroxide, bismuth subsalicylate, calcium carbonate, calcium hydroxide, calcium phosphate, dihydroxyaluminum sodium carbonate, magnesium hydroxide, magnesium oxide, magnesium trisilicate, sodium bicarbonate, simethicone, glycine, or combinations thereof.

Where present, other co-administered pharmaceutical agents can be employed, for example, in formulations as described above and in amounts and dosing as indicated in the Physician's Desk Reference (PDR), as indicated in the prescribing information approved by a government regulatory agency (e.g., Food and Drug Administration, FDA or European Medicines Agency, EMEA), as recommended by the innovator of the agent or as recommend by a healthcare provider.

In some embodiments, 25-desacetyl rifaximin, for example, purified or isolated 25-desacetyl rifaximin, or a pharmaceutically acceptable salt, solvate or hydrate thereof is administered to the subject in a pharmaceutically-acceptable formulation. In certain embodiments, 25-desacetyl rifaximin or a pharmaceutically acceptable salt, solvate or hydrate thereof or a 25-desacetyl rifaximin pharmaceutical composition is suitable for topical, intravenous, parental, or oral administration. The methods further include administering to a subject a therapeutically effective amount of 25-desacetyl rifaximin or a pharmaceutically acceptable salt, solvate or hydrate thereof.

The 25-desacetyl rifaximin can be administered in the dosage forms as described herein in single or divided doses of, for example, one to four times daily. It can be advisable to start a patient on a low dose and work up gradually to a high dose combination.

The phrase "pharmaceutically acceptable" refers to purified or isolated 25-desacetyl rifaximin, compositions containing purified or isolated 25-desacetyl rifaximin, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, involved in carrying or transporting the subject chemical from one organ, or portion of the body, to another organ, or portion of the body. Each carrier is "acceptable" in the sense of being compatible with the other ingredients of the formulation and not injurious to the patient.

Methods of preparing these compositions include bringing into association 25-desacetyl rifaximin or a pharmaceutically acceptable salt, solvate or hydrate thereof and a carrier and, optionally, one or more accessory ingredients. These compositions can also contain adjuvants such as preservatives, wetting agents, emulsifying agents and dispersing agents.

Regardless of the route of administration selected, 25-desacetyl rifaximin, which can be used in a suitable salt, solvate, or hydrate form, and/or the pharmaceutical compositions of 25-desacetyl rifaximin, are formulated into pharmaceutically acceptable dosage forms by methods known to those of skill in the art.

Formulations are provided to a subject in an effective amount. The term "effective amount" includes an amount effective, at dosages and for periods of time necessary, to achieve the desired result. An effective amount of purified or isolated 25-desacetyl rifaximin can vary according to factors such as the disease state, age, and weight of the subject, and the ability of the compound to elicit a desired response in the subject. An effective amount of 25-desacetyl rifaximin can vary according to other factors such as intended travel destination of a subject, including for example, Latin America, Africa, the Middle East, and Asia, including both developed, undeveloped and developing areas therein. An effective amount of 25-desacetyl rifaximin can vary according other risk-factors a subject can have including, for example, young age, advanced age, immunosuppression, diagnosis of inflammatory-bowel disease or diabetes, and prior treatment with H-2 blockers or antacids. Dosage regimens can be adjusted to provide the optimum therapeutic response.

The effective amount is generally determined by the physician on a case-by-case basis and is within the skill of one in the art. As a rule, the dosage for in vivo therapeutics or diagnostics will vary. Several factors, among others, can be taken into account when determining an appropriate dosage. These factors include age, sex and weight of the patient, the condition being treated, and the severity of the condition. The length of treatment for a particular bowel disorder will depend, in part, on the disorder. For example, travelers' diarrhea may only require treatment duration of 12 to about 72 hours, while Crohn's disease may require treatment durations from about 2 days to 3 months. Hepatic encephalopathy may be treated for the remainder of a subject's life after diagnosis. IBS, for example, can be treated for two weeks to two months or longer. Subjects can also be retreated with 25-desacetyl rifaximin as necessary. Dosages of rifaximin will also vary depending on the diseases state. Exemplary dosage ranges are provided herein infra.

The identification of those subjects who are in need of prophylactic treatment for bowel disorder is well within the ability and knowledge of one skilled in the art. Certain of the methods for identification of subjects which are at risk of developing a bowel disorder which can be treated by the subject method are appreciated in the medical arts, such as family history, travel history and expected travel plans, the presence of risk factors associated with the development of that disease state in the subject. A clinician skilled in the art can readily identify such candidate subjects, by the use of, for example, clinical tests, physical examination and medical/family/travel history.

Suitable dosages and formulations of 25-desacetyl rifaximin or a pharmaceutically acceptable salt, solvate or hydrate thereof can be empirically determined by the administering physician. Standard texts, such as Remington: The Science and Practice of Pharmacy, 17th edition, Mack Publishing Company, and the Physician's Desk Reference, each of which are incorporated herein by reference, can be consulted to prepare suitable compositions and doses for administration. A determination of the appropriate dosage is within the skill of one in the art given the parameters for use described herein.

Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

In terms of treatment, an effective amount is an amount that is sufficient to palliate, ameliorate, stabilize, reverse or slow the progression of one or more bowel related disorders or enteric infections, the symptoms of any thereof, or to reduce the symptoms of pain, gas, bloating or flatulence. A therapeutically effective amount can be provided in one or a series of administrations. The effective amount is generally determined by the physician on a case-by-case basis and is within the skill of one in the art.

As a rule, the dosage for in vivo therapeutics or diagnostics will vary. Several factors may be taken into account when determining an appropriate dosage. These factors include, for example, age, sex and weight of the patient, the condition being treated, and the severity of the condition.

The dosage of 25-desacetyl rifaximin or a pharmaceutically acceptable salt, solvate or hydrate thereof can vary from about 10 mg to about 10 g per day; about 20 mg to about 5 g per day; about 50 mg to about 2 g per day; or about 100 mg to about 600 mg per day. Dosages between these ranges are also included herein, for example, a dosage of 1650 mg/day or a dosage of 1100 mg/day. Ascertaining dosage ranges is well within the skill of one in the art. The dosage of 25-desacetyl rifaximin or a pharmaceutically acceptable salt, solvate or hydrate thereof can range from about 0.05 to 150 mg/kg of body weight. Such dosages can vary, for example, depending on whether multiple administrations are given, tissue type and route of administration, the condition of the individual, the desired objective and other factors known to those of skill in the art. Administrations can be conducted infrequently, or on a regular weekly basis until a desired, measurable parameter is detected, such as diminution of disease symptoms. Administration can then be diminished, such as to a biweekly or monthly basis, as appropriate.

A therapeutically effective amount can be administered in one or more doses. The term "administration" or "administering" includes routes of introducing the compound(s) to a subject to perform their intended function. Examples of routes of administration which can be used include injection (subcutaneous, intravenous, parenterally, intraperitoneally, intrathecal), oral, inhalation, rectal and transdermal.

The phrases "parenteral administration" and "administered parenterally" as used herein means modes of administration other than enteral and topical administration, for example, by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

Available routes of administration include subcutaneous, intramuscular, intraperitoneal, intradermal, oral, intranasal, intrapulmonary (e.g., by aerosol), intravenously, intramuscularly, subcutaneously, intracavity, intrathecally or transdermally, alone or in combination with other pharmaceutical agents.

25-desacetyl rifaximin or a pharmaceutically acceptable salt, solvate or hydrate thereof and compositions comprising 25-desacetyl rifaximin that are suitable for oral administration can be presented as discrete dosage forms, such as, for example, tablets (e.g., chewable tablets), caplets, capsules, and liquids (e.g., flavored syrups). Such dosage forms contain predetermined amounts of active ingredients, and can be prepared by methods of pharmacy well known to those skilled in the art. See generally, *Remington's Pharmaceutical Sciences,* 18*th ed.*, Mack Publishing, Easton Pa. (1990).

Oral dosage forms can be prepared, for example, by combining the active ingredient(s) in an intimate admixture with at least one excipient. Excipients can take a wide variety of forms depending on the form of preparation desired for administration. For example, excipients suitable for use in oral liquid or aerosol dosage forms include, for example, water, glycols, oils, alcohols, flavoring agents, preservatives, and coloring agents. Examples of excipients suitable for use in solid oral dosage forms (e.g., powders, tablets, capsules, and caplets) include, for example, starches, sugars, microcrystalline cellulose, diluents, granulating agents, lubricants, binders, and disintegrating agents. If desired, tablets can be coated by standard aqueous or nonaqueous techniques. Such dosage forms can be prepared by any of the methods of pharmacy.

Examples of excipients that can be used in oral dosage forms include, for example for example, binders, fillers, disintegrants, and lubricants. Binders suitable for use in pharmaceutical compositions and dosage forms include, for example, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., nos. 2208, 2906, 2910), microcrystalline cellulose, and mixtures thereof.

Examples of fillers suitable for use in the pharmaceutical compositions and dosage forms disclosed herein include, for example, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions may, for example, be present from about 50 to about 99 weight percent of the pharmaceutical composition or dosage form.

Suitable forms of microcrystalline cellulose include, for example, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103.™ and Starch 1500 LM.

Disintegrants can be used to provide tablets that disintegrate when exposed to an aqueous environment. Compositions herein can comprise from about 0.5 to about 15 weight percent of disintegrant, specifically from about 1 to about 5 weight percent of disintegrant.

Lubricants that can be used in pharmaceutical compositions and dosage forms described herein can include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof.

Parenteral and intravascular dosage forms can be administered to subjects by various routes including, for example, subcutaneous, intravenous (including bolus injection and constant infusion), intramuscular, and intraarterial. Examples of parenteral dosage forms include, for example, solutions ready for injection, dry products (including, for example lyophilized powders, pellets, and tablets) ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, for example: Water for Injection USP; aqueous vehicles such as, for example, Sodium Chloride Injection, Ringer's Injection, Dextrose Injection, Dextrose and Sodium Chloride Injection, and Lactated Ringer's Injection; water-miscible vehicles such as, for example, ethyl alcohol, polyethylene glycol, and polypropylene glycol; and non-aqueous vehicles such as, for example, corn oil, cottonseed oil, peanut oil, sesame oil, ethyl oleate, isopropyl myristate, and benzyl benzoate.

Transdermal, topical, and mucosal dosage forms can include, for example, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients. Dosage forms can also be administered in the form of suppositories for rectal administration of the drug. These compositions can be prepared by mixing the compound with a suitable non-irritation excipient which is solid at ordinary temperatures but liquid at the rectal temperature and will therefore melt in the rectum to release the compound. Such materials are, for example, cocoa butter and polyethylene glycol.

Depending on the specific tissue to be treated, additional components can be used prior to, in conjunction with, or subsequent to treatment with 25-desacetyl rifaximin. For example, penetration enhancers can be used to assist in delivering the active ingredients to the tissue. Suitable penetration enhancers include, for example: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Although methods and materials similar or equivalent to those described herein can be used in the composition described herein, certain methods and materials are described herein. The materials, methods, and examples are illustrative only and not intended to be limiting. Other features and advantages of the 25-desacetyl rifaximin and compositions thereof will be apparent from the detailed description and from the claims.

Kits

Provided herein are kits which, when used by the medical practitioner, can simplify the identification of subjects and the administration of appropriate amounts of 25-desacetyl rifaximin and/or a pharmaceutically acceptable salt, solvate or hydrate thereof to a patient.

One kit provided herein comprises one or more unit dosage forms of 25-desacetyl rifaximin or a pharmaceutically acceptable salt, solvate or hydrate thereof, and instructions for identification of a subject.

Kits can further comprise devices that are used to administer 25-desacetyl rifaximin or a pharmaceutically acceptable salt, solvate or hydrate thereof. Examples of such devices include, for example, intravenous cannulation devices, syringes, drip bags, patches, topical gels, pumps, containers that provide protection from photodegredation, autoinjectors, and inhalers.

Kits can further comprise pharmaceutically acceptable vehicles that can be used to administer one or more active ingredients. For example, if an active ingredient is provided in a solid form that is reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, for example: Water for Injection USP; aqueous vehicles such as, for example for example, Sodium Chloride Injection, Ringer's Injection, Dextrose Injection, Dextrose and Sodium Chloride Injection, and Lactated Ringer's Injection; water-miscible vehicles such as, for example, ethyl alcohol, polyethylene glycol, and polypropylene glycol; and non-aqueous vehicles such as, for example, corn oil, cottonseed oil, peanut oil, sesame oil, ethyl oleate, isopropyl myristate, and benzyl benzoate.

EXAMPLES

To more fully understand the 25-desacetyl rifaximin and compositions thereof, the following examples are provided. It should be understood that these examples are for illustrative purposes only and are not to be construed as limiting in any way.

Example 1

Preparation of 25-Desacetyl Rifaximin

A reaction to prepare 25-Desacetyl Rifaximin was carried out according to Scheme 1 shown below.

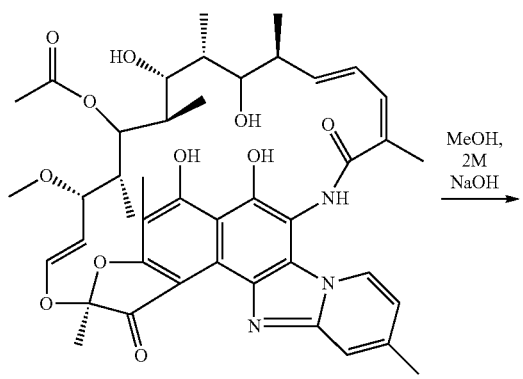

Molecular Weight = 785.90
Exact Mass = 785
Molecular Formula = C43H51N3O11
Molecular Composition = C 65.72% H 6.54% N 5.35% O 22.39%

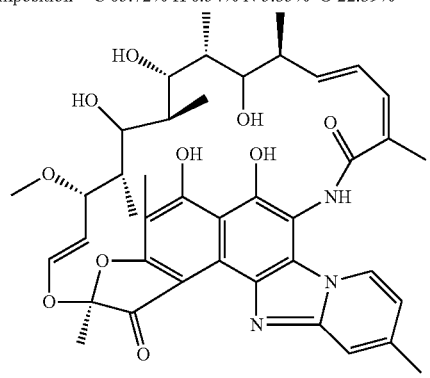

Molecular Weight = 743.86
Exact Mass = 743
Molecular Formula = C41H49N3O10
Molecular Composition = C 66.20% H 6.64% N 5.65% O 21.51%

Removal of the 25-acetyl moiety using 2M NaOH in methanol proceeded smoothly at room temperature. Acidification of the mixture to pH=4 gave the desired 25-desacetyl rifaximin. Initial small scale experiments indicated that water is beneficial to producing filterable solids, thus dilute HCl (1 M in water) was used to acidify the mixture. Purification of the crude material (~95% AUC) was accomplished by trituration of the crude solid with water/methanol (2:1), giving product with an HPLC purity of 97.9% (AUC).

Rifaximin (100 g, 0.127 moles, 1 eq.) was added to a stirring solution of MeOH at room temperature (18-21° C.) and stirred for 5 minutes. A 2M NaOH solution (318 mL, 0.636 moles, 5 eq) was added over 2-3 min and the mixture turns from an orange suspension to a darker colored solution. The reaction mixture was stirred 3 h at ambient temperature (19-25° C.) after which time HPLC analysis shows little or no starting material. The reaction was quenched by adjusting the pH of the mixture to pH=4 using 1M HCl, while maintaining the temperature below 30° C. The resultant suspension was stirred at ambient temperature (19-27° C.) for 1.5 h then filtered through a Buchner funnel and washed with $H_2O$ (2×50 mL) followed by 2×100 mL of MTBE and lastly 50 mL of EtOAc. The crude orange-brown solid was dried in a vacuum oven (35-40° C., >29.5" Hg) to give 79 g of crude 25-desacetyl rifaximin.

Crude des-acetyl rifaximin (75 g) was suspended in 375 mL of $H_2O$/MeOH (2:1) and stirred for 1 h. The mixture was filtered and the solids were washed with $H_2O$ (70 mL) followed by MTBE (70 mL), then dried in a vacuum oven (18-20° C., >29.5" Hg) overnight (17 h) to give 70.5 g of purified des-acetyl rifaximin (HPLC Purity (AUC)=97.9%, LC/MS (M+)=744.

Rifaximin can also be desacetylated to 25 desacetyl rifaximin using any desacetylation techniques known in the art. The desacetylation can be accomplished by hydrolyzing the $CH_2COO$ group linked to $C_{25}$ of the rifaximin molecules. The hydrolysis process can be accomplished by treating the rifaximin dissolved in a suitable alkaline solvent. The alkalizing agents include, for example, hydroxides, organic bases, bicarbonates, and the like.

Example 2

Bacterial Activity Assays

| Bacteria | Compound | Class | Dose | Criteria | Results |
|---|---|---|---|---|---|
| *Enterococcus faecalis* (VRE, ATCC 51575) | 25-desacetyl rifaximin | Gram Positive | 10 µg/mL | +/− | + |
| | Rifaximin | Gram Positive | 10 µg/mL | +/− | + |
| *Escherichia coli* (ATCC 10536) | Rifaximin | Gram Negative | 3 µg/mL | +/− | + |
| *Escherichia coli* (ATCC 25922) | Rifaximin | Gram Negative | 10 µg/mL | +/− | + |
| *Escherichia coli* (Juhl) | Rifaximin | Gram Negative | 10 µg/mL | +/− | + |
| *Enterobacter cloacae* (ATCC 13047) | Rifaximin | Gram Negative | 100 µg/mL | +/− | + |
| *Pseudomonas aeruginosa* (ATCC 9027) | Rifaximin | Gram Negative | 10 µg/mL | +/− | + |
| *Clostridium sporogenes* (ATCC 7955) | 25-desacetyl rifaximin | Anaerobes | 1 µg/mL | +/− | + |
| *Clostridium sporogenes* (ATCC 7955) | Rifaximin | Anaerobes | 0.03 µg/mL | +/− | + |
| *Clostridium defficile* (ATCC 9689) | 25-desacetyl rifaximin | Anaerobes | 0.3 µg/mL | +/− | + |
| | Rifaximin | Anaerobes | 0.03 µg/mL | +/− | + |
| *Clostridium perfringens* (ATCC 13124) | 25-desacetyl rifaximin | Anaerobes | 0.03 µg/mL | +/− | + |
| | Rifaximin | Anaerobes | 0.03 µg/mL | +/− | + |
| *Helicobacter pylori* (ATCC 43504) | Rifaximin | Anaerobes | 3 µg/mL | +/− | + |

| Bacteria | Compound | Class | Route | N = | Concentration | Criteria | Result |
|---|---|---|---|---|---|---|---|
| *Bacteroides fragilis* (ATCC 23745) | 25-desacetyl rifaximin 1141022 | Anaerobes | in vitro | 2 | 100 µg/mL | +/− | − |
| | | | | 2 | 30 µg/mL | +/− | − |
| | | | | 2 | 10 µg/mL | +/− | − |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| | Rifaximin 1141023 | Anaerobes | in vitro | 2 | 100 µg/mL | +/− | − |
| | | | | 2 | 30 µg/mL | +/− | − |
| | | | | 2 | 10 µg/mL | +/− | − |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| *Clostridium difficile* (ATCC 9689) | ··25-desacetyl rifaximin 1141022 | Anaerobes | in vitro | 2 | 100 µg/mL | +/− | + |
| | ··25-desacetyl rifaximin 1141022 | | | 2 | 30 µg/mL | +/− | + |
| | ··25-desacetyl rifaximin 1141022 | | | 2 | 10 µg/mL | +/− | + |
| | ··25-desacetyl rifaximin 1141022 | | | 2 | 3 µg/mL | +/− | + |
| | ··25-desacetyl rifaximin 1141022 | | | 2 | 1 µg/mL | +/− | + |
| | ··25-desacetyl rifaximin 1141022 | | | 2 | 0.3 µg/mL | +/− | + |
| | | | | 2 | 0.1 µg/mL | +/− | − |
| | | | | 2 | 0.03 µg/mL | +/− | − |
| | ··Rifaximin 1141023 | Anaerobes | in vitro | 2 | 100 µg/mL | +/− | + |
| | ··Rifaximin 1141023 | | | 2 | 30 µg/mL | +/− | + |
| | ··Rifaximin 1141023 | | | 2 | 10 µg/mL | +/− | + |
| | ··Rifaximin 1141023 | | | 2 | 3 µg/mL | +/− | + |
| | ··Rifaximin 1141023 | | | 2 | 1 µg/mL | +/− | + |
| | ··Rifaximin 1141023 | | | 2 | 0.3 µg/mL | +/− | + |
| | ··Rifaximin 1141023 | | | 2 | 0.1 µg/mL | +/− | + |
| | ··Rifaximin 1141023 | | | 2 | 0.03 µg/mL | +/− | + |
| *Clostridium perfringens* (ATCC 13124) | ··25-desacetyl rifaximin 1141022 | Anaerobes | in vitro | 2 | 100 µg/mL | +/− | + |
| | ··25-desacetyl rifaximin 1141022 | | | 2 | 30 µg/mL | +/− | + |
| | ··25-desacetyl rifaximin 1141022 | | | 2 | 10 µg/mL | +/− | + |
| | ··25-desacetyl rifaximin 1141022 | | | 2 | 3 µg/mL | +/− | + |

-continued

| Bacteria | Compound | Class | Route | N = | Concentration | Criteria | Result |
|---|---|---|---|---|---|---|---|
| | ¨25-desacetyl rifaximin 1141022 | | | 2 | 1 µg/mL | +/− | + |
| | ¨25-desacetyl rifaximin 1141022 | | | 2 | 0.3 µg/mL | +/− | + |
| | ¨25-desacetyl rifaximin 1141022 | | | 2 | 0.1 µg/mL | +/− | + |
| | ¨25-desacetyl rifaximin 1141022 | | | 2 | 0.03 µg/mL | +/− | + |
| | ¨Rifaximin 1141023 | Anaerobes | in vitro | 2 | 100 µg/mL | +/− | + |
| | ¨Rifaximin 1141023 | | | 2 | 30 µg/mL | +/− | + |
| | ¨Rifaximin 1141023 | | | 2 | 10 µg/mL | +/− | + |
| | ¨Rifaximin 1141023 | | | 2 | 3 µg/mL | +/− | + |
| | ¨Rifaximin 1141023 | | | 2 | 1 µg/mL | +/− | + |
| | ¨Rifaximin 1141023 | | | 2 | 0.3 µg/mL | +/− | + |
| | ¨Rifaximin 1141023 | | | 2 | 0.1 µg/mL | +/− | + |
| | ¨Rifaximin 1141023 | | | 2 | 0.03 µg/mL | +/− | + |
| 620500 Clostridium sporogenes (ATCC 7955) | ¨25-desacetyl rifaximin 1141022 | Anaerobes | in vitro | 2 | 100 µg/mL | +/− | + |
| | ¨25-desacetyl rifaximin 1141022 | | | 2 | 30 µg/mL | +/− | + |
| | ¨25-desacetyl rifaximin 1141022 | | | 2 | 10 µg/mL | +/− | + |
| | ¨25-desacetyl rifaximin 1141022 | | | 2 | 3 µg/mL | +/− | + |
| | ¨25-desacetyl rifaximin 1141022 | | | 2 | 1 µg/mL | +/− | + |
| | | | | 2 | 0.3 µg/mL | +/− | − |
| | | | | 2 | 0.1 µg/mL | +/− | − |
| | | | | 2 | 0.03 µg/mL | +/− | − |
| | ¨Rifaximin 1141023 | Anaerobes | in vitro | 2 | 100 µg/mL | +/− | + |
| | ¨Rifaximin 1141023 | | | 2 | 30 µg/mL | +/− | + |
| | ¨Rifaximin 1141023 | | | 2 | 10 µg/mL | +/− | + |
| | ¨Rifaximin 1141023 | | | 2 | 3 µg/mL | +/− | + |
| | ¨Rifaximin 1141023 | | | 2 | 1 µg/mL | +/− | + |
| | ¨Rifaximin 1141023 | | | 2 | 0.3 µg/mL | +/− | + |
| | ¨Rifaximin 1141023 | | | 2 | 0.1 µg/mL | +/− | + |
| | ¨Rifaximin 1141023 | | | 2 | | +/− | + |

-continued

| Bacteria | Compound | Class | Route | N = | Concentration | Criteria | Result |
|---|---|---|---|---|---|---|---|
| 611500 Enterobacter cloacae (ATCC 13047) | 25-desacetyl rifaximin | Gram Negative | in vitro | 2 | 100 µg/mL | +/− | − |
| | | | | 2 | 30 µg/mL | +/− | − |
| | | | | 2 | 10 µg/mL | +/− | − |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| | Rifaximin | Gram Negative | in vitro | 2 | 100 µg/mL | +/− | + |
| | | | | 2 | 30 µg/mL | +/− | − |
| | | | | 2 | 10 µg/mL | +/− | − |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| 602100 Enterococcus faecalis (VRE, ATCC 51575) | 25-desacetyl rifaximin | Gram Positive | in vitro | 2 | 100 µg/mL | +/− | + |
| | | | | 2 | 30 µg/mL | +/− | + |
| | | | | 2 | 10 µg/mL | +/− | + |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| | Rifaximin | Gram Positive | in vitro | 2 | 100 µg/mL | +/− | + |
| | | | | 2 | 30 µg/mL | +/− | + |
| | | | | 2 | 10 µg/mL | +/− | + |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| 610000 Escherichia coli (ATCC 10536) | 25-desacetyl rifaximin | Gram Negative | in vitro | 2 | 100 Ug/mL | +/− | − |
| | | | | 2 | 30 µg/mL | +/− | − |
| | | | | 2 | 10 µg/mL | +/− | − |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| | Rifaximin | Gram Negative | in vitro | 2 | 100 µg/mL | +/− | + |
| | Rifaximin | | | 2 | 30 µg/mL | +/− | + |
| | Rifaximin | | | 2 | 10 µg/mL | +/− | + |
| | Rifaximin | | | 2 | 3 µg/mL | +/− | + |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| 610100 Escherichia coli (ATCC 25922) | 25-desacetyl rifaximin | Gram Negative | in vitro | 2 | 100 Ug/mL | +/− | − |
| | | | | 2 | 30 µg/mL | +/− | − |
| | | | | 2 | 10 µg/mL | +/− | − |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |
| | Rifaximin | Gram Negative | in vitro | 2 | 100 µg/mL | +/− | + |
| | Rifaximin | | | 2 | 30 µg/mL | +/− | + |
| | Rifaximin | | | 2 | 10 µg/mL | +/− | + |
| | | | | 2 | 3 µg/mL | +/− | − |
| | | | | 2 | 1 µg/mL | +/− | − |
| | | | | 2 | 0.3 µg/mL | +/− | − |
| | | | | 2 | 0.1 µg/mL | +/− | − |
| | | | | 2 | 0.03 µg/mL | +/− | − |

-continued

| Bacteria | Compound | Class | Route | N = | Concentration | Criteria | Result |
|---|---|---|---|---|---|---|---|
| 611000 Escherichia coli (Juhl) | 25-desacetyl rifaximin 1141021 | Gram Negative | in vitro | 2 | 100 μg/mL | +/− | − |
| | | | | 2 | 30 μg/mL | +/− | − |
| | | | | 2 | 10 μg/mL | +/− | − |
| | | | | 2 | 3 μg/mL | +/− | − |
| | | | | 2 | 1 μg/mL | +/− | − |
| | | | | 2 | 0.3 μg/mL | +/− | − |
| | | | | 2 | 0.1 μg/mL | +/− | − |
| | | | | 2 | 0.03 μg/mL | +/− | − |
| | ¨Rifaximin 1141022 | Gram Negative | in vitro | 2 | 100 μg/mL | +/− | + |
| | ¨Rifaximin 1141022 | | | 2 | 30 μg/mL | +/− | + |
| | ¨Rifaximin 1141022 | | | 2 | 10 μg/mL | +/− | + |
| | | | | 2 | 3 μg/mL | +/− | − |
| | | | | 2 | 1 μg/mL | +/− | − |
| | | | | 2 | 0.3 μg/mL | +/− | − |
| | | | | 2 | 0.1 μg/mL | +/− | − |
| | | | | 2 | 0.03 μg/mL | +/− | − |
| 621500 Helicobacter pylori (ATCC 43504) | 25-desacetyl rifaximin | Anaerobes | in vitro | 2 | 100 μg/mL | +/− | − |
| | | | | 2 | 30 μg/mL | +/− | − |
| | | | | 2 | 10 μg/mL | +/− | − |
| | | | | 2 | 3 μg/mL | +/− | − |
| | | | | 2 | 1 μg/mL | +/− | − |
| | | | | 2 | 0.3 μg/mL | +/− | − |
| | | | | 2 | 0.1 μg/mL | +/− | − |
| | | | in vitro | 2 | 0.03 μg/mL | +/− | − |
| | ¨Rifaximin | Anaerobes | | 2 | 100 μg/mL | +/− | + |
| | ¨Rifaximin | | | 2 | 30 μg/mL | +/− | + |
| | ¨Rifaximin | | | 2 | 10 μg/mL | +/− | + |
| | ¨Rifaximin | | | 2 | 3 μg/mL | +/− | + |
| | | | | 2 | 1 μg/mL | +/− | − |
| | | | | 2 | 0.3 μg/mL | +/− | − |
| | | | | 2 | 0.1 μg/mL | +/− | − |
| | | | in vitro | 2 | 0.03 μg/mL | +/− | − |
| 614000 Pseudomonas aeruginosa (ATCC 9027) | 25-desacetyl rifaximin | Gram Negative | in vitro | 2 | 100 μg/mL | +/− | − |
| | | | | 2 | 30 μg/mL | +/− | − |
| | | | | 2 | 10 μg/mL | +/− | − |
| | | | | 2 | 3 μg/mL | +/− | − |
| | | | | 2 | 1 μg/mL | +/− | − |
| | | | | 2 | 0.3 μg/mL | +/− | − |
| | | | | 2 | 0.1 μg/mL | +/− | − |
| | | | | 2 | 0.03 μg/mL | +/− | − |
| | ¨Rifaximin | Gram Negative | in vitro | 2 | 100 μg/mL | +/− | + |
| | ¨Rifaximin | | | 2 | 30 μg/mL | +/− | + |
| | ¨Rifaximin | | | 2 | 10 μg/mL | +/− | + |
| | | | | 2 | 3 μg/mL | +/− | − |
| | | | | 2 | 1 μg/mL | +/− | − |
| | | | | 2 | 0.3 μg/mL | +/− | − |
| | | | | 2 | 0.1 μg/mL | +/− | − |
| | | | | 2 | 0.03 μg/mL | +/− | − |

| 620000 Bacteroides fragilis (ATCC 23745) | |
|---|---|
| Culture Medium: | Reinforced Clostridial Medium |
| Vehicle: | 1% DMSO |
| Incubation Time/Temp: | 2 days at 37° C. |
| Incubation Volume: | 1 mL |
| Time of Assessment: | 2 days |
| Quantitation Method: | Turbidity Measurement |

| 620600 Clostridium defficile (ATCC 9689) | |
|---|---|
| Culture Medium: | Reinforced Clostridial Medium |
| Vehicle: | 1% DMSO |
| Incubation Time/Temp: | 2 days at 37° C. |
| Incubation Volume: | 3 mL |
| Time of Assessment: | 2 days |
| Quantitation Method: | Turbidity Measurement |

| 620700 Clostridium perfringens (ATCC 13124) | |
|---|---|
| Culture Medium: | Reinforced Clostridial Medium |
| Vehicle: | 1% DMSO |
| Incubation Time/Temp: | 2 days at 37° C. |
| Incubation Volume: | 3 mL |
| Time of Assessment: | 2 days |
| Quantitation Method: | Turbidity Measurement |

| 620500 Clostridium sporogenes (ATCC 7955) | |
|---|---|
| Culture Medium: | Reinforced Clostridial Medium |
| Vehicle: | 1% DMSO |
| Incubation Time/Temp: | 2 days at 37° C. |
| Incubation Volume: | 3 mL |
| Time of Assessment: | 2 days |
| Quantitation Method: | Turbidity Measurement |

| 611500 Enterobacter cloacae (ATCC 13047) | |
|---|---|
| Culture Medium: | Mueller-Hinton Broth |
| Vehicle: | 1% DMSO |
| Incubation Time/Temp: | 20 hours at 37° C. |
| Incubation Volume: | 1 mL |
| Time of Assessment: | 1 day |
| Quantitation Method: | Turbidity Measurement |

| 602100 Enterococcus faecalis (VRE, ATCC 51575) | |
|---|---|
| Culture Medium: | Tryptic Soy Broth with 7% FBS |
| Vehicle: | 1% DMSO |
| Incubation Time/Temp: | 20 hours at 37° C. |
| Incubation Volume: | 1 mL |
| Time of Assessment: | 1 day |
| Quantitation Method: | Turbidity Measurement |

| 610000 Escherichia coli (ATCC 10536) | |
|---|---|
| Culture Medium: | Mueller-Hinton Broth |
| Vehicle: | 1% DMSO |
| Incubation Time/Temp: | 20 hours at 37° C. |
| Incubation Volume: | 1 mL |
| Time of Assessment: | 1 day |
| Quantitation Method: | Turbidity Measurement |

| 610100 Escherichia coli (ATCC 25922) | |
|---|---|
| Culture Medium: | Mueller-Hinton Broth |
| Vehicle: | 1% DMSO |
| Incubation Time/Temp: | 20 hours at 37° C. |
| Incubation Volume: | 1 mL |
| Time of Assessment: | 1 day |
| Quantitation Method: | Turbidity Measurement |

| 611000 Escherichia coli (Juhl) | |
|---|---|
| Culture Medium: | Mueller-Hinton Broth |
| Vehicle: | 1% DMSO |
| Incubation Time/Temp: | 20 hours at 37° C. |
| Incubation Volume: | 1 mL |
| Time of Assessment: | 1 day |
| Quantitation Method: | Turbidity Measurement |

| 621500 Helicobacter pylori (ATCC 43504) | |
|---|---|
| Culture Medium: | Columbia Agar Base + 7% defibrinated rabbit blood |
| Vehicle: | 1% DMSO |
| Incubation Time/Temp: | 2 days at 37° C. |
| Incubation Volume: | 1 mL |
| Time of Assessment: | 4 days |
| Quantitation Method: | Inhibition of colony growth was read |

| 614000 Pseudomonas aeruginosa (ATCC 9027) | |
|---|---|
| Culture Medium: | Mueller-Hinton Broth |
| Vehicle: | 1% DMSO |
| Incubation Time/Temp: | 20 hours at 37° C. |
| Incubation Volume: | 1 mL |
| Time of Assessment: | 1 day |
| Quantitation Method: | Turbidity Measurement |

In Vitro Activity of Rifaximin and 25-Desacetyl Rifaximin

The in vitro activities of rifaximin and 25-desacetyl rifaximin are shown in the tables below (e.g., Tables 2, 3, and 4) as a range of Minimum Inhibitory Concentration (MIC) values encountered and $MIC_{50}$ and $MIC_{90}$.

TABLE 2a

Activity against Enterobacteriaceae spp. strains

| Antimicrobial Agent | Range (mg/L) | $MIC_{50}$ (mg/L) | $MIC_{90}$ (mg/L) | Mode (mg/L) |
|---|---|---|---|---|
| Rifaximin | 8-32 | 32 | 32 | 32 |
| 25-Desacetyl rifaximin | 128-256 | 128 | 256 | 128 |

TABLE 2b

Activity against Enterobacteriaceae spp. strains

| | | MIC (mg/L) | |
|---|---|---|---|
| N. | Strains | Rifaximin | 25-Desacetyl rifaximin |
| 1 | ATCC E. Coli 25922 | 16 | 128 |
| 2 | C. freundii 57 | 16 | 128 |
| 3 | C. freundii 58 | 32 | 128 |
| 4 | C. freundii 65 | 32 | 128 |
| 5 | C. freundii 68 | 32 | 256 |
| 6 | C. freundii 69 | 32 | 128 |
| 7 | C. freundii 1070 | 32 | 128 |
| 8 | C. freundii 1073 | 32 | 256 |
| 9 | C. freundii 1075 | 32 | 128 |
| 10 | E. aerogenes 235 | 32 | 128 |
| 11 | E. aerogenes 281 | 32 | 128 |
| 12 | E. aerogenes 290 | 32 | 128 |
| 13 | E. aerogenes 1023 | 32 | 128 |
| 14 | E. aerogenes 1030 | 32 | 256 |
| 15 | E. aerogenes 1031 | 32 | 128 |
| 16 | E. cloacae 3 | 32 | 128 |
| 17 | E. cloacae 1 | 32 | 128 |
| 18 | E. cloacae 8 | 32 | 256 |
| 19 | E. cloacae 12 | 32 | 128 |
| 20 | E. cloacae 13 | 32 | 128 |
| 21 | E. cloacae 14 | 32 | 128 |
| 22 | E. cloacae 16 | 32 | 128 |
| 23 | E. cloacae 20 | 32 | 128 |
| 24 | E. cloacae 321 | 32 | 128 |
| 25 | E. cloacae 348 | 32 | 256 |
| 26 | E. cloacae 349 | 32 | 128 |
| 27 | E. cloacae 358 | 32 | 128 |
| 28 | E. cloacae 367 | 32 | 128 |
| 29 | E. cloacae 369 | 32 | 256 |
| 30 | E. sacazakii 9 | 32 | 128 |
| 31 | E. sacazakii 11 | 32 | 128 |
| 32 | E. sacazakii 104 | 32 | 128 |

TABLE 2b-continued

Activity against Enterobacteriaceae spp. strains

| N. | Strains | MIC (mg/L) Rifaximin | MIC (mg/L) 25-Desacetyl rifaximin |
|---|---|---|---|
| 33 | E. coli 6 | 32 | 128 |
| 34 | E. coli 15 | 16 | 128 |
| 35 | E. coli 34 | 32 | 128 |
| 36 | E. coli 37 | 8 | 128 |
| 37 | E. coli 41 | 16 | 128 |
| 38 | E. coli 43 | 16 | 128 |
| 39 | E. coli 44 | 16 | 256 |
| 40 | E. coli 46 | 16 | 128 |
| 41 | E. coli 47 | 32 | 128 |
| 42 | E. coli 48 | 32 | 256 |
| 43 | E. coli 49 | 32 | 128 |
| 44 | E. coli 56 | 32 | 128 |
| 45 | E. coli 62 | 32 | 128 |
| 46 | E. coli 71 | 8 | 128 |
| 47 | E. coli 90 | 16 | 128 |
| 48 | E. coli 92 | 32 | 128 |
| 49 | E. coli 93 | 32 | 256 |
| 50 | E. coli 95 | 32 | 128 |
| 51 | E. coli 96 | 8 | 128 |
| 52 | E. coli 97 | 32 | 128 |
| 53 | E. coli 100 | 32 | 128 |
| 54 | E. coli 102 | 16 | 128 |
| 55 | E. coli 103 | 32 | 128 |
| 56 | E. coli 109 | 32 | 128 |
| 57 | E. coli 110 | 32 | 256 |
| 58 | E. coli 112 | 32 | 128 |
| 59 | E. coli 113 | 32 | 128 |
| 60 | E. coli 117 | 16 | 256 |
| 61 | E. coli 118 | 32 | 128 |
| 62 | E. coli 120 | 32 | 128 |
| 63 | E. coli 140 | 32 | 256 |
| 64 | E. coli 171 | 32 | 128 |
| 65 | E. coli 342 | 32 | 128 |
| 66 | E. coli 343 | 32 | 256 |
| 67 | E. coli 345 | 32 | 128 |
| 68 | E. coli 349 | 32 | 128 |
| 69 | E. coli 351 | 32 | 128 |
| 70 | K. pneumoniae 17 | 32 | 128 |
| 71 | K. pneumoniae 19 | 32 | 128 |
| 72 | K. pneumoniae 76 | 32 | 256 |
| 73 | K. pneumoniae 80 | 32 | 128 |
| 74 | K. pneumoniae 91 | 32 | 128 |
| 75 | K. pneumoniae 1064 | 32 | 128 |
| 76 | K. oxytoca 4 | 32 | 128 |
| 77 | K. oxytoca 18 | 32 | 128 |
| 78 | K. oxytoca 479 | 32 | 128 |
| 79 | K. oxytoca 499 | 32 | 128 |
| 80 | M. morganii 42 | 16 | 128 |
| 81 | M. morganii 48 | 32 | 128 |
| 82 | M. morganii 50 | 32 | 128 |
| 83 | M. morganii 57 | 32 | 256 |
| 84 | M. morganii 67 | 32 | 256 |
| 85 | M. morganii 101 | 32 | 128 |
| 86 | M. morganii 105 | 32 | 128 |
| 87 | M. morganii 108 | 32 | 128 |
| 88 | M. morganii 453 | 8 | 128 |
| 89 | M. morganii 458 | 32 | 256 |
| 90 | M. morganii 461 | 32 | 128 |
| 91 | M. morganii 462 | 32 | 128 |
| 92 | M. morganii 923 | 16 | 128 |
| 93 | M. morganii 932 | 32 | 128 |
| 94 | M. morganii 935 | 32 | 256 |
| 95 | M. morganii 1006 | 8 | 128 |
| 96 | P. mirabilis 465 | 32 | 128 |
| 97 | P. mirabilis 466 | 32 | 128 |
| 98 | P. mirabilis 469 | 32 | 128 |
| 99 | P. mirabilis 470 | 16 | 128 |
| 100 | P. mirabilis 471 | 8 | 256 |
| 101 | P. mirabilis 472 | 8 | 128 |
| 102 | P. mirabilis 473 | 16 | 128 |
| 103 | P. mirabilis 477 | 32 | 128 |
| 104 | P. mirabilis 479 | 32 | 128 |
| 105 | P. mirabilis 480 | 32 | 256 |
| 106 | P. mirabilis 489 | 32 | 128 |
| 107 | P. mirabilis 928 | 32 | 128 |
| 108 | P. mirabilis 972 | 32 | 128 |
| 109 | P. mirabilis 983 | 16 | 128 |
| 110 | P. mirabilis 985 | 32 | 256 |
| 111 | P. mirabilis 987 | 32 | 128 |
| 112 | P. mirabilis 988 | 8 | 128 |
| 113 | P. mirabilis 990 | 32 | 128 |
| 114 | P. mirabilis 991 | 32 | 128 |
| 115 | P. mirabilis 993 | 16 | 128 |
| 116 | P. mirabilis 995 | 32 | 128 |
| 117 | P. mirabilis 996 | 32 | 128 |
| 118 | P. mirabilis 997 | 32 | 128 |
| 119 | P. mirabilis 998 | 8 | 256 |
| 120 | P. stuartii 94 | 32 | 128 |
| 121 | P. stuartii 299 | 16 | 128 |
| 122 | P. stuartii 301 | 32 | 128 |
| 123 | P. stuartii 306 | 16 | 256 |
| 124 | P. stuartii 312 | 32 | 128 |
| 125 | P. stuartii 459 | 32 | 128 |
| 126 | S. liquefaciens 53 | 32 | 128 |
| 127 | S. liquefaciens 55 | 32 | 256 |
| 128 | S. marcescens 38 | 32 | 128 |
| 129 | S. marcescens 45 | 32 | 128 |
| 130 | S. marcescens 59 | 32 | 128 |
| 131 | S. marcescens 63 | 32 | 256 |
| 132 | S. odorifera 52 | 32 | 128 |
| 133 | S. odorifera 59 | 32 | 128 |
| 134 | S. maltophilia 1203 | 32 | 128 |
| 135 | S. maltophilia 1208 | 32 | 128 |

TABLE 3a

Activity against Staphylococcus spp. strains

| Antimicrobial Agent | Range (mg/L) | MIC$_{50}$ (mg/L) | MIC$_{90}$ (mg/L) | Mode (mg/L) |
|---|---|---|---|---|
| Rifaximin | 0.03-1 | 0.25 | 1 | 0.5 |
| 25-Desacetyl rifaximin | 0.12->16 | 2 | 16 | 2 |

TABLE 3b

Activity against Staphylococcus spp. strains

| N. | Strains | MIC (mg/L) Rifaximin | MIC (mg/L) 25-Desacetyl rifaximin |
|---|---|---|---|
| 1 | ATCC S. aureus 29213 | 0.015 | 0.5 |
| 2 | S. aureus 215 | 1 | 16 |
| 3 | S. aureus 234 | 0.25 | 2 |
| 4 | S. aureus 236 | 1 | 16 |
| 5 | S. aureus 237 | 0.06 | 2 |
| 6 | S. aureus 238 | 0.03 | 0.25 |
| 7 | S. aureus 246 | 0.5 | 2 |
| 8 | S. aureus 252 | 0.5 | 4 |
| 9 | S. aureus 253 | 0.12 | 1 |
| 10 | S. aureus 267 | 1 | 16 |
| 11 | S. aureus 272 | 0.25 | 2 |
| 12 | S. aureus 279 | 0.03 | 0.25 |
| 13 | S. aureus 327 | 1 | 4 |
| 14 | S. aureus 328 | 0.5 | 2 |
| 15 | S. aureus 329 | 1 | 4 |
| 16 | S. aureus 339 | 1 | 16 |
| 17 | S. aureus 345 | 0.25 | 2 |
| 18 | S. aureus 355 | 0.5 | 2 |

TABLE 3b-continued

Activity against *Staphylococcus* spp. strains

| | | MIC (mg/L) | |
|---|---|---|---|
| N. | Strains | Rifaximin | 25-Desacetyl rifaximin |
| 19 | S. aureus 406 | 0.5 | >16 |
| 20 | S. aureus 408 | 0.25 | 2 |
| 21 | S. aureus 409 | 0.12 | 1 |
| 22 | S. aureus 416 | 0.5 | 2 |
| 23 | S. aureus 425 | 0.5 | >16 |
| 24 | S. aureus 436 | 0.06 | 2 |
| 25 | S. aureus 475 | 0.5 | 4 |
| 26 | S. epidermidis 332 | 0.06 | 0.12 |
| 27 | S. epidermidis 354 | 0.06 | 0.12 |
| 28 | S. haemolyticus 243 | 0.06 | 0.5 |
| 29 | S. haemolyticus 276 | 0.12 | 1 |
| 30 | S. haemolyticus 955 | 0.12 | 1 |
| 31 | S. haemolyticus 982 | 0.06 | 0.5 |
| 32 | S. xylosus 337 | 0.5 | 2 |
| 33 | S. xylosus 346 | 0.5 | 2 |
| 34 | S. spp. 1102 | 0.06 | 1 |
| 35 | S. spp. 1187 | 0.03 | 2 |
| 36 | S. spp. 1195 | 0.06 | 0.12 |
| 37 | S. spp. 1256 | 0.12 | 4 |
| 38 | S. spp. 1312 | 0.25 | 4 |
| 39 | S. spp. 1689 | 1 | 4 |
| 40 | S. spp. 1745 | 0.06 | 0.25 |

TABLE 4a

Activity against *Enterococcus* spp. strains

| Antimicrobial Agent | Range (mg/L) | MIC$_{50}$ (mg/L) | MIC$_{90}$ (mg/L) | Mode (mg/L) |
|---|---|---|---|---|
| Rifaximin | 2->16 | 8 | >16 | 4 |
| 25-Desacetyl rifaximin | 4->16 | >16 | >16 | >16 |

TABLE 4b

Activity against *Enterococcus* spp. strains

| | | MIC (mg/L) | |
|---|---|---|---|
| N. | Strains | Rifaximin | 25-Desacetyl rifaximin |
| 1 | ATCC E. faecalis 29212 | 4 | 16 |
| 2 | E. faecalis 181 | 4 | >16 |
| 3 | E. faecalis 186 | 4 | 4 |
| 4 | E. faecalis 187 | 4 | 4 |
| 5 | E. faecalis 193 | 4 | 4 |
| 6 | E. faecalis 194 | 4 | >16 |
| 7 | E. faecalis 200 | >16 | >16 |
| 8 | E. faecalis 204 | 4 | 4 |
| 9 | E. faecalis 205 | 4 | >16 |
| 10 | E. faecalis 210 | 4 | 4 |
| 11 | E. faecalis 227 | >16 | >16 |
| 12 | E. faecalis 228 | 4 | 4 |
| 13 | E. faecalis 232 | 4 | 4 |
| 14 | E. faecalis 235 | 16 | >16 |
| 15 | E. faecalis 237 | 4 | 4 |
| 16 | E. faecalis 239 | 8 | >16 |
| 17 | E. faecalis 242 | >16 | >16 |
| 18 | E. faecalis 243 | 16 | >16 |
| 19 | E. faecalis 245 | >16 | >16 |
| 20 | E. faecalis 249 | 4 | 4 |
| 21 | E. faecalis 250 | 4 | >16 |
| 22 | E. faecalis 251 | 8 | >16 |
| 23 | E. faecalis 255 | 4 | 4 |
| 24 | E. faecium 8 | 4 | 4 |
| 25 | E. faecium 13 | 4 | 4 |
| 26 | E. faecium 174 | 8 | >16 |

TABLE 4b-continued

Activity against *Enterococcus* spp. strains

| | | MIC (mg/L) | |
|---|---|---|---|
| N. | Strains | Rifaximin | 25-Desacetyl rifaximin |
| 27 | E. faecium 185 | >16 | >16 |
| 28 | E. faecium 188 | 8 | >16 |
| 29 | E. faecium 189 | 4 | 8 |
| 30 | E. faecium 190 | 16 | >16 |
| 31 | E. faecium 191 | >16 | >16 |
| 32 | E. faecium 192 | 2 | 8 |
| 33 | E. faecium 198 | 16 | >16 |
| 34 | E. faecium 199 | 8 | >16 |
| 35 | E. faecium 201 | 16 | >16 |
| 36 | E. faecium 203 | 4 | 8 |
| 37 | E. faecium 207 | 4 | >16 |
| 38 | E. faecium 208 | 2 | 4 |
| 39 | E. faecium 209 | 16 | >16 |
| 40 | E. faecium 212 | >16 | >16 |
| 41 | E. faecium 215 | >16 | >16 |
| 42 | E. faecium 217 | 8 | 4 |
| 43 | E. faecium 221 | 8 | >16 |
| 44 | E. faecium 222 | >16 | >16 |
| 45 | E. faecium 223 | >16 | >16 |
| 46 | E. faecium 225 | 4 | >16 |
| 47 | E. faecium 229 | 2 | 8 |
| 48 | E. faecium 230 | 8 | 4 |
| 49 | E. faecium 231 | 16 | >16 |
| 50 | E. faecium 236 | 2 | 4 |
| 51 | E. faecium 238 | 16 | >16 |
| 52 | E. faecium 240 | >16 | >16 |
| 53 | E. faecium 248 | >16 | >16 |

Radioligand Binding Assays—the Activity of 25-Desacetyl Rifaximin

Methods employed in this study have been adapted from the scientific literature to maximize reliability and reproducibility. Reference standards were run as an integral part of each assay to ensure the validity of the results obtained. Assays were performed under conditions described in the accompanying "Methods" section below. The literature reference(s) for each assay are in the "Literature References" section.

Where presented, IC$_{50}$ values were determined by a non-linear, least squares regression analysis using MathIQ™ (ID Business Solutions Ltd., UK). Where inhibition constants (K$_I$) are presented, the K$_I$ values were calculated using the equation of Cheng and Prusoff (Cheng, Y., Prusoff, W. H., Biochem. Pharmacol. 22:3099-3108, 1973) using the observed IC$_{50}$ of the tested compound, the concentration of radioligand employed in the assay, and the historical values for the K$_D$ of the ligand (obtained experimentally at Ricerca Biosciences, LLC). Where presented, the Hill coefficient (n$_H$), defining the slope of the competitive binding curve, was calculated using MathIQ™. Hill coefficients significantly different than 1.0 may suggest that the binding displacement does not follow the laws of mass action with a single binding site. Where IC$_{50}$, K$_I$, and/or n$_H$ data are presented without Standard Error of the Mean (SEM), data are insufficient to be quantitative, and the values presented (K$_I$, IC$_{50}$, n$_H$) should be interpreted with caution.

Significant results are displayed in the following table(s) in rank order of potency for estimated IC$_{50}$ and/or K$_I$ values.

Biochemical assay results are presented as the percent inhibition of specific binding or activity throughout the report. All other results are expressed in terms of that assay's quantitation method (see Methods section). For primary assays, only the lowest concentration with a significant response judged by the assays' criteria, is shown in this summary.

Where applicable, either the secondary assay results with the lowest dose/concentration meeting the significance criteria or, if inactive, the highest dose/concentration that did not meet the significance criteria is shown.

Unless otherwise requested, primary screening in duplicate with quantitative data (e.g., IC50±SEM, Ki±SEM and nH) are shown where applicable for individual requested assays. In screening packages, primary screening in duplicate with semi-quantitative data (e.g., estimated IC50, Ki and nH) are shown where applicable (concentration range of 4 log units); available secondary functional assays are carried out (30 mM) and MEC or MIC determined only if active in primary assays>50% at 1 log unit below initial test concentration. Significant responses (50% inhibition or stimulation for Biochemical assays) were noted in the primary assays listed below:

| PRIMARY BIOCHEMICAL ASSAY | SPECIES | CONC. | % INH. |
|---|---|---|---|
| Bombesin BB1 | hum | 10 µM | 53 |
| N-Formyl Peptide Receptor FPR1 | hum | 10 µM | 54 |

As shown above, each of rifaximin and 25-desacetyl rifaximin were screened at 10 µM against 168 targets; a screen was considered significant if a 50% effect (either inhibition or stimulation) was observed. For 25-desacetyl, there were two "hits": Bombesin BB1 and N-formyl peptide receptor FPR1—each achieved just over 50% inhibition. No hits were reported for rifaximin (although potency against bombesin and FPR1 appear to be just below the 50% threshold).

Accordingly, provided herein are method of inhibiting Bombesin BB1 by administering 25-desacetyl rifaximin. Also provided herein are methods of inhibiting N-formyl peptide receptor FPR1 by administering 25-desacetyl rifaximin.

Those skilled in the art will recognize, or be able to ascertain using no more than routine experimentation, many equivalents to the specific embodiments described herein. Such equivalents are intended to be encompassed by the following claims.

All references cited herein, whether in print, electronic, computer readable storage media or other form, are expressly incorporated by reference in their entirety and may be employed in the practice of the invention, including for example, abstracts, articles, journals, publications, texts, treatises, technical data sheets, manufacturer's instructions, descriptions, product specifications, product sheets, internet web sites, databases, patents, patent applications, and patent publications.

We claim:

1. A method for treating irritable bowel syndrome, travelers' diarrhea, small intestinal bacterial overgrowth, or hepatic encephalopathy, comprising administering to a subject in need thereof a therapeutically effective amount of 25-desacetyl rifaximin having the formula:

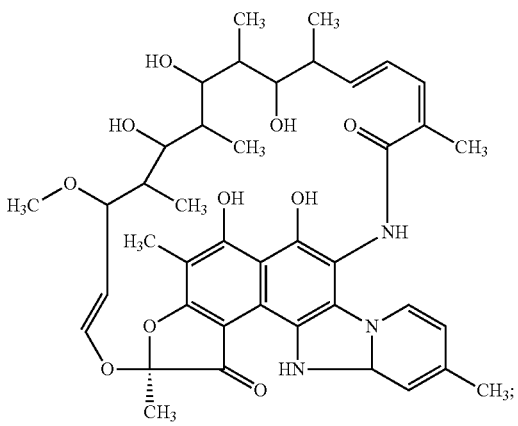 [SMILES: COC1/C=C/O[C@@]2(C)Oc3c(C)c(O)c4c(O)c(c5c(c4c3C2=O)NC2C=C(C)C=CN52)NC(=O)/C(C)=C\C=C\C(C)C(O)C(C)C(O)C(C)C(O)C1C]

or a pharmaceutically acceptable salt thereof.

2. The method of claim 1, wherein the traveler's diarrhea is caused by exposure to one or more enteric pathogens.

3. The method of claim 2, wherein the one or more enteric pathogens is selected from *Salmonella* spp., *Shigella* spp., *Campylobacter* spp., *Aeromonas, Plesiomonas, Vibro* spp., *Yersinia entercolitica, E. coli*, Enterotoxigenic *Escherichia coli* (ETEC), *E. coli* 0157:H7, *C. difficile* and *H. pylori*.

4. The method of claim 2, wherein the enteric pathogens comprise one or more of a gram-positive bacteria, a gram-negative bacteria, an aerobic bacteria or an anaerobic bacteria.

5. The method of claim 3, wherein *E. coli* comprises enterotoxigenic and/or enteroaggregative strains.

6. The method of claim 1, further comprising administering rehydration therapy (RT) to the subject.

7. The method of claim 6, wherein the RT is administered before, during and/or after the administration of the 25-desacetyl rifaximin.

8. The method of claim 6, wherein the RT comprises one or more of oral rehydration therapy or intravenous rehydration therapy.

* * * * *